United States Patent
Mordaunt

(10) Patent No.: US 10,806,536 B2
(45) Date of Patent: Oct. 20, 2020

(54) PHYSICIAN-SAFE ILLUMINATION IN OPHTHALMIC SURGERIES

(71) Applicant: EOS HOLDINGS LLC, Los Gatos, CA (US)

(72) Inventor: David Mordaunt, Los Gatos, CA (US)

(73) Assignee: EOS Holdings, LLC, Los Gatos, CA (US)

(*) Notice: Subject to any disclaimer, the term of this patent is extended or adjusted under 35 U.S.C. 154(b) by 0 days.

(21) Appl. No.: 14/931,611

(22) Filed: Nov. 3, 2015

(65) Prior Publication Data
US 2017/0119490 A1    May 4, 2017

(51) Int. Cl.
*A61B 3/10* (2006.01)
*A61B 3/00* (2006.01)
*G02B 27/10* (2006.01)
*A61B 90/30* (2016.01)

(52) U.S. Cl.
CPC ............ *A61B 90/30* (2016.02); *A61B 3/0008* (2013.01); *A61B 3/10* (2013.01); *G02B 27/1006* (2013.01); *A61B 2090/306* (2016.02); *A61B 2090/309* (2016.02)

(58) Field of Classification Search
CPC ... A61B 3/0008; A61B 1/0646; A61B 1/0653; A61B 2018/00636; G02B 27/10; G02B 27/1006; G02B 27/102
USPC ....... 351/221; 600/249; 606/11, 12; 359/629
See application file for complete search history.

(56) References Cited

U.S. PATENT DOCUMENTS

| | | | | |
|---|---|---|---|---|
| 3,760,174 A * | 9/1973 | Boenning | ............... | H04N 1/502 315/312 |
| 4,071,809 A * | 1/1978 | Weiss | ................. | G02B 27/1006 315/312 |
| 7,682,027 B2 * | 3/2010 | Buczek | ................. | A61B 90/36 351/221 |
| 8,348,430 B2 * | 1/2013 | Artsyukhovich | .... | A61B 3/0008 351/221 |
| 8,610,088 B2 * | 12/2013 | Westphal | .................. | F21V 9/08 250/484.4 |
| 8,699,138 B2 * | 4/2014 | Cogger | .................. | G02B 21/06 359/290 |
| 2006/0055885 A1 | 3/2006 | Mizuno | | |

(Continued)

FOREIGN PATENT DOCUMENTS

WO    2011/150431 A1    12/2011
WO    2014/145465 A2    9/2014

OTHER PUBLICATIONS

Kuse, Yoshiki; et al. "Damage of Photoreceptor-Derived Cells in Culture Induced by Light Emitting Diode-Derived Blue Light." Scientific Reports, vol. 4, ser. 5223, Jun. 9, 2014, pp. 1-12. 5223, doi:10.1038/srep05223.*

(Continued)

*Primary Examiner* — Zachary W Wilkes
(74) *Attorney, Agent, or Firm* — Innovation Counsel LLP

(57) ABSTRACT

Apparatus and methods combine light emitted by a narrow band laser having a peak emission wavelength greater than or equal to about 480 nm with light emitted from one or more additional light sources to provide an illumination beam for illumination inside a human or animal during a diagnostic or surgical procedure. The narrow band laser provides the shortest wavelength contribution to the illumination beam.

9 Claims, 8 Drawing Sheets

(56) References Cited

U.S. PATENT DOCUMENTS

| | | | |
|---|---|---|---|
| 2008/0212191 A1* | 9/2008 | Harle | G02B 27/143 |
| | | | 359/618 |
| 2009/0185251 A1 | 7/2009 | Chen et al. | |
| 2010/0177280 A1 | 7/2010 | Buczek et al. | |
| 2010/0228089 A1 | 9/2010 | Hoffman et al. | |
| 2011/0149246 A1* | 6/2011 | Artsyukhovich | A61B 3/0008 |
| | | | 351/221 |
| 2011/0149247 A1* | 6/2011 | Artsyukhovich | A61B 3/0008 |
| | | | 351/221 |
| 2011/0208004 A1 | 8/2011 | Feingold et al. | |
| 2011/0299034 A1 | 12/2011 | Walsh et al. | |
| 2014/0128686 A1 | 5/2014 | Klaffenbach et al. | |
| 2015/0366443 A1* | 12/2015 | Liolios | A61F 9/00821 |
| | | | 600/249 |
| 2017/0343792 A1* | 11/2017 | Matsunobu | G02B 19/0047 |

OTHER PUBLICATIONS

Lang, Marion. "Lasers for Confocal Microscopy." GIT Imaging & Microscopy, 2011, pp. 41-42; iChrome MLE. TOPTICA Photonics, May 5, 2019, www.toptica.com/products/multi-laser-engines/ichrome-mle/.*

* cited by examiner

PHYSICIAN-SAFE ILLUMINATION IN OPHTHALMIC SURGERIES

FIELD OF THE INVENTION

The invention relates generally to illumination in diagnostic and surgical procedures inside a human or animal, for example illumination in ophthalmic diagnostic and surgical procedures.

BACKGROUND

Ophthalmic surgical and diagnostic procedures generally require that the tissue (e.g., the retina) that is the target of the procedure be visualized through a microscope or other optical apparatus. Such visualization typically requires illumination of the tissue, for example with light provided through an optical fiber probe or chandelier inserted into the patient's eye. Generally, it is desirable that the illuminating light appear white or tinted-white to the medical practitioner ("physician" as used herein) who is performing the procedure, to facilitate visualization of the target tissue. It is also generally recognized that it is desirable to avoid damaging the target tissue, or other tissue in the patient's eye, with the illuminating light. Such damage may occur for example through photochemical mechanisms typically driven by blue or violet light at the short wavelength end of the visible spectrum or by ultraviolet light, or through thermal mechanisms. Ophthalmic illumination systems may therefore utilize combinations of light sources and filters designed to provide illumination that will not damage the patient's tissue during the typical duration of a few minutes for a diagnostic procedure or 10 to 200 minutes for a surgical procedure. The largest risk for the patient is when the illumination light exiting the delivery device is in close proximity to tissue, such as the retina. Risk to the physician's eyes from exposure to the illumination used in visualizing the target tissue has generally received less attention.

SUMMARY

Applicant has recognized that the risk to a physician's eyes from exposure to illumination from ophthalmic or other endoillumination apparatus may be significant, because it may accumulate over the course of numerous diagnostic or surgical procedures performed during the course of a work day, which may amount to a much longer duration of exposure for the physician than for any single patient. In part to address this risk to the physician, this specification discloses physician-safe apparatus and methods in which the shortest wavelength contribution to an illumination light beam is provided by a narrow band laser having a peak wavelength greater than or equal to about 480 nanometers (nm). The output from this laser is combined with light at longer wavelengths provided by one or more additional light sources to form the illumination beam. Restricting the shortest wavelength light in the illumination beam to wavelengths greater than or equal to about 480 nm may significantly improve physician safety compared to previous illumination systems using shorter wavelength light. The light in the ophthalmic illumination beam may, for example, appear white or tinted white to a human having normal color vision.

The physician-safe light sources disclosed herein are described below with respect to ophthalmic applications. However, these light sources may also be used for example in endoscopic procedures to illuminate internal portions of the colon or of the esophagus, in coronary diagnostic and surgical procedures performed using catheters, in other minimally invasive procedures employing catheters, and in any other suitable medical and dental procedures.

These and other embodiments, features and advantages of the present invention will become more apparent to those skilled in the art when taken with reference to the following more detailed description of the invention in conjunction with the accompanying drawings that are first briefly described.

DETAILED DESCRIPTION

Figure 1:
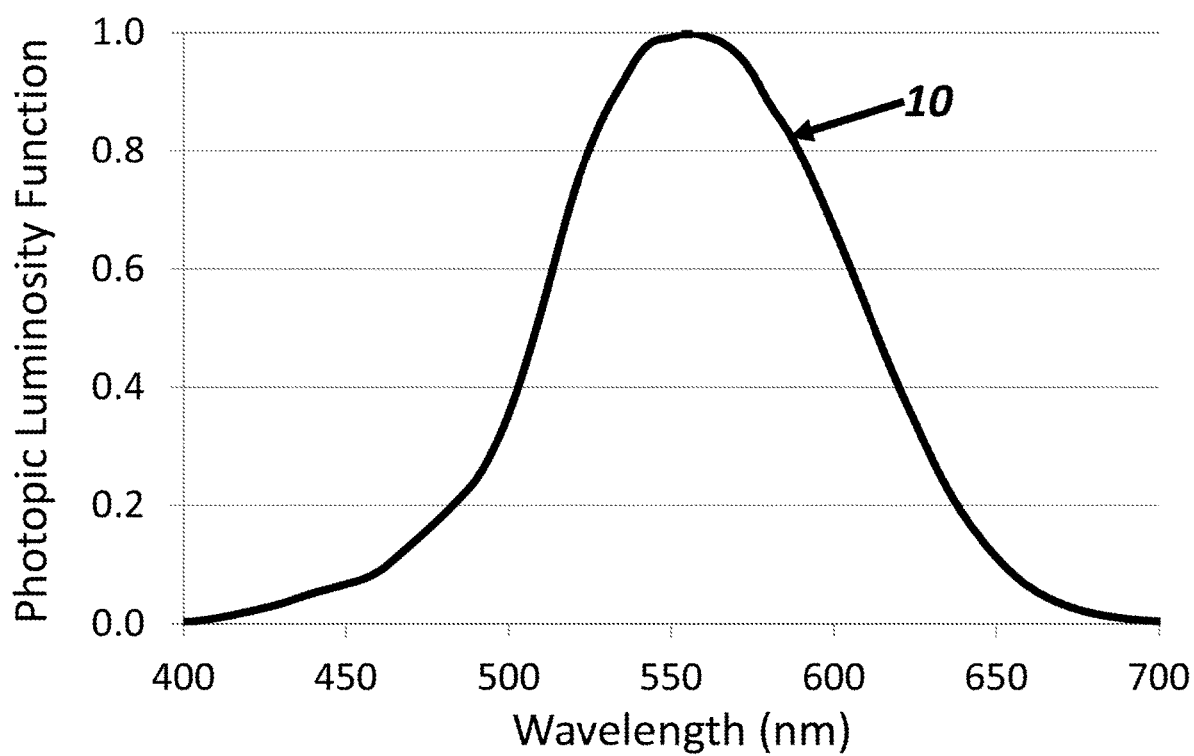
FIG. 1 shows a plot of the photopic luminosity function.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used in this specification and the appended claims, the singular forms "a," "an," and "the" include plural referents unless the context clearly indicates otherwise.

This specification discloses physician and patient-safe ophthalmic illumination apparatus and methods that reduce or minimize blue-light phakic retinal hazard for physicians and reduce or minimize aphakic retinal hazard for patients. Phakic hazard refers to risk of damage to an eye from light passing through all of the optical elements of the intact eye, including the cornea and the lens. Aphakic hazard refers to risk of damage to an eye from light that does not pass through the lens and cornea of the eye, but is for example introduced into the eye through an optical fiber probe. The aphakic and phakic hazard functions are the same for wavelengths $\lambda > 435$ nm. At 435 nm and shorter wavelengths the aphakic and phakic hazard functions differ because the cornea and lens absorb some of the blue, violet, and ultraviolet light.

In the physician and patient-safe ophthalmic illumination apparatus and methods disclosed herein, the shortest wavelength contribution to the illumination beam is provided by a laser (e.g., a laser diode) having narrow band emission around a peak wavelength greater than or equal to about 480 nm (for example, a peak wavelength in the range 480 nm to 495 nm). The output from this laser is combined with light from one or more additional light sources emitting at longer wavelengths than those emitted by this laser to form the illumination beam. The emission peak of the λ≥480 nm laser may have a full width at half maximum of about 2 nm to about 10 nm, for example. The 480 nm to 495 nm wavelength region may also be referred to herein as being azure in color. Azure is centered at the halfway point between blue (450 nm-495 nm) and cyan (495 nm-520 nm).

The one or more additional light sources contributing to the illumination beam may include, for example, another laser having narrow band emission in the green portion of the visible spectrum and/or another laser having narrow band emission in the red portion of the visible spectrum. Alternatively, the one or more additional light sources may include one or more light-emitting diodes (LEDs), for example a green LED and/or a red LED and/or an orange LED.

Because the shortest wavelength light source contributing to the illumination beam has narrow band peak emission at λ≥480 nm, blue light phakic retinal hazard to the physician is reduced without interposing a spectrum-distorting blue light filter in the optical path between the patient's eye and the physician's eyes or using an undesirably low-power blue contribution to the illumination beam. Consequently, the combined emission from the λ≥480 nm laser and the one or more other longer wavelength light sources may provide a white or tinted-white illumination beam as viewed by the physician.

The portion of the emission from the physician-safe ophthalmic illuminators disclosed herein at wavelengths less than 480 nm may be, for example, less than or equal to about 10% of the total emission, less than or equal to about 3% of the total emission, less than or equal to about 1.0% of the total emission, or less than or equal to about 0.2% of the total emission.

The choice of light sources and emission wavelengths used to form the illumination beam may be optimized considering the photopic luminosity function (the eye's detection sensitivity to light as a function of wavelength), the photochemical blue light retinal hazard function, and/or the transmission characteristics of any optical filter (e.g., a narrow band notch filter) interposed in the optical path between the patient's eye and the physician's eyes to protect the physician's eyes from light from a therapeutic (treatment) laser beam used to perform a surgical procedure in the patient's eye.

Therapeutic laser beams may have narrow emission spectra centered, for example at about 532 nm, at about 561 nm, or at about 577 nm. A notch filter used to protect the physician from the therapeutic beam would typically have a stop band approximately centered on the therapeutic laser beam wavelength. To prevent the notch filter from spectrally distorting the illumination beam, as viewed by the physician, the light sources contributing to the ophthalmic illumination beam may be selected to have low or no emission in the wavelength range of the notch filter stop band, i.e., high transmittance through the notch filter.

Figure 2:
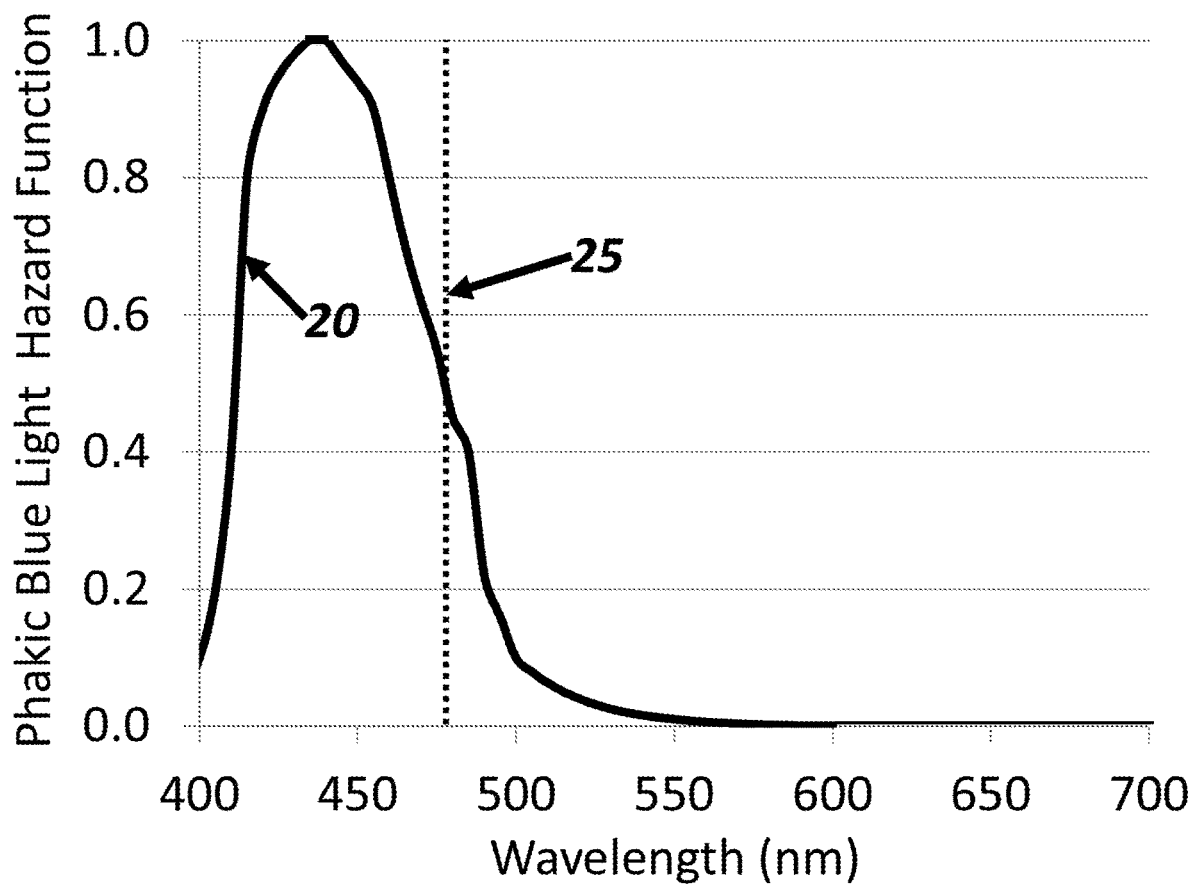
FIG. 2 shows a plot of the phakic blue light retinal hazard function.

FIG. 1 shows a plot of the photopic luminosity function 10. FIG. 2 shows a plot of the phakic blue light retinal hazard function 20, with a vertical line 25 indicating the location of 480 nm on the horizontal axis. As apparent in FIG. 2, this hazard function is steeper (increases more quickly as wavelength decreases) at wavelengths shorter than about 480 nm than at wavelengths greater than about 480 nm, i.e., there is a kink in the hazard curve at about 480 nm. The blue light phakic retinal hazard function is reported in Table 1 of "International Commission on Non-Ionizing Radiation Protection. Guidelines on limits of exposure to broad-band incoherent optical radiation (0.38 to 3 microns)", published in Health Phys 1997; 73:539-54.

Figure 3:
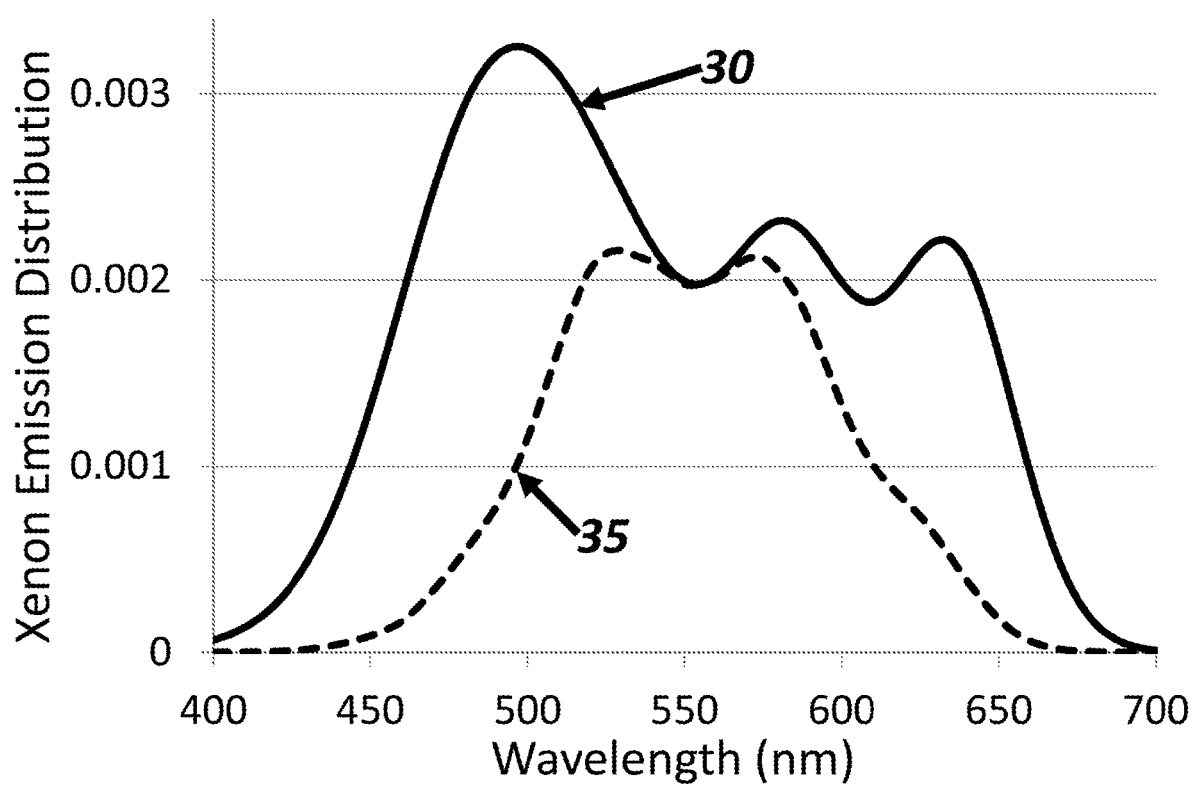
FIG. 3 shows a plot of the emission spectrum from a xenon ophthalmic illumination light source and a plot of the photopically corrected emission spectrum.
Figure 4:
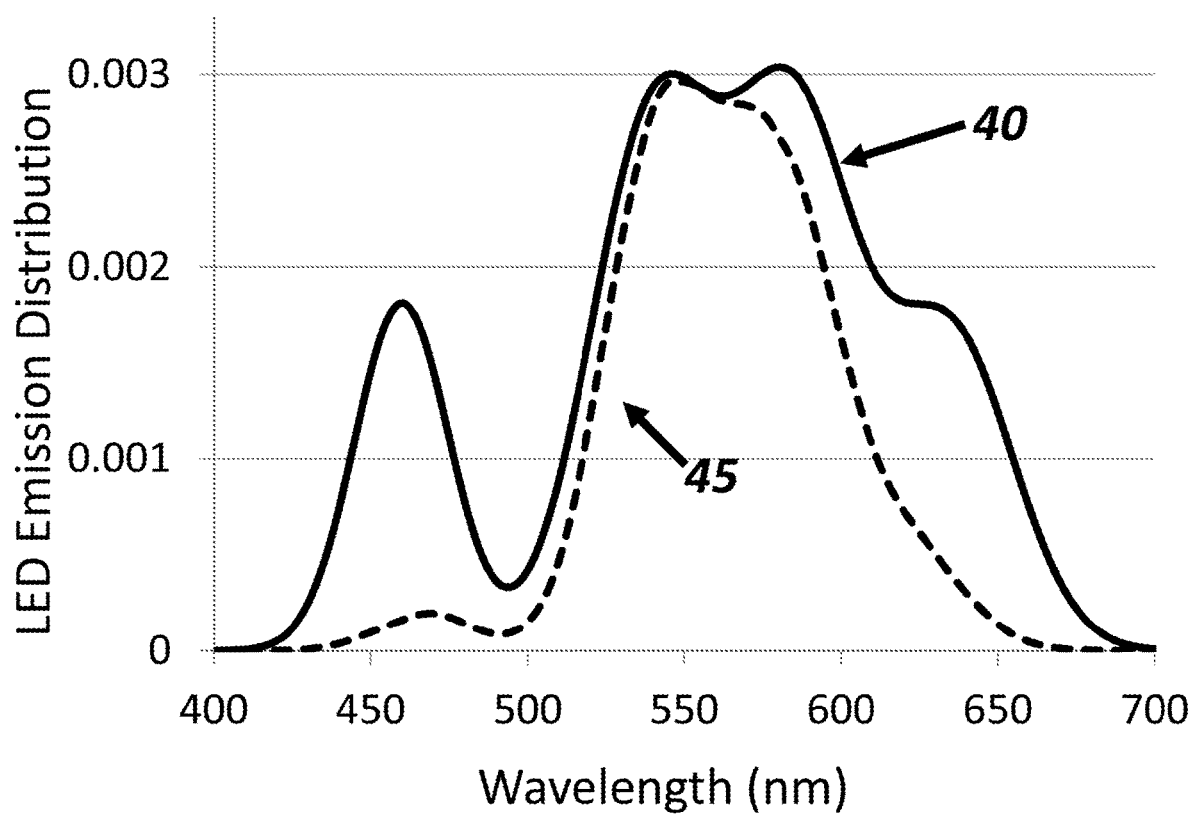
FIG. 4 shows a plot of the emission spectrum from an ophthalmic illumination light source that uses four LEDs and a plot of the photopically corrected emission spectrum.
Figure 5:
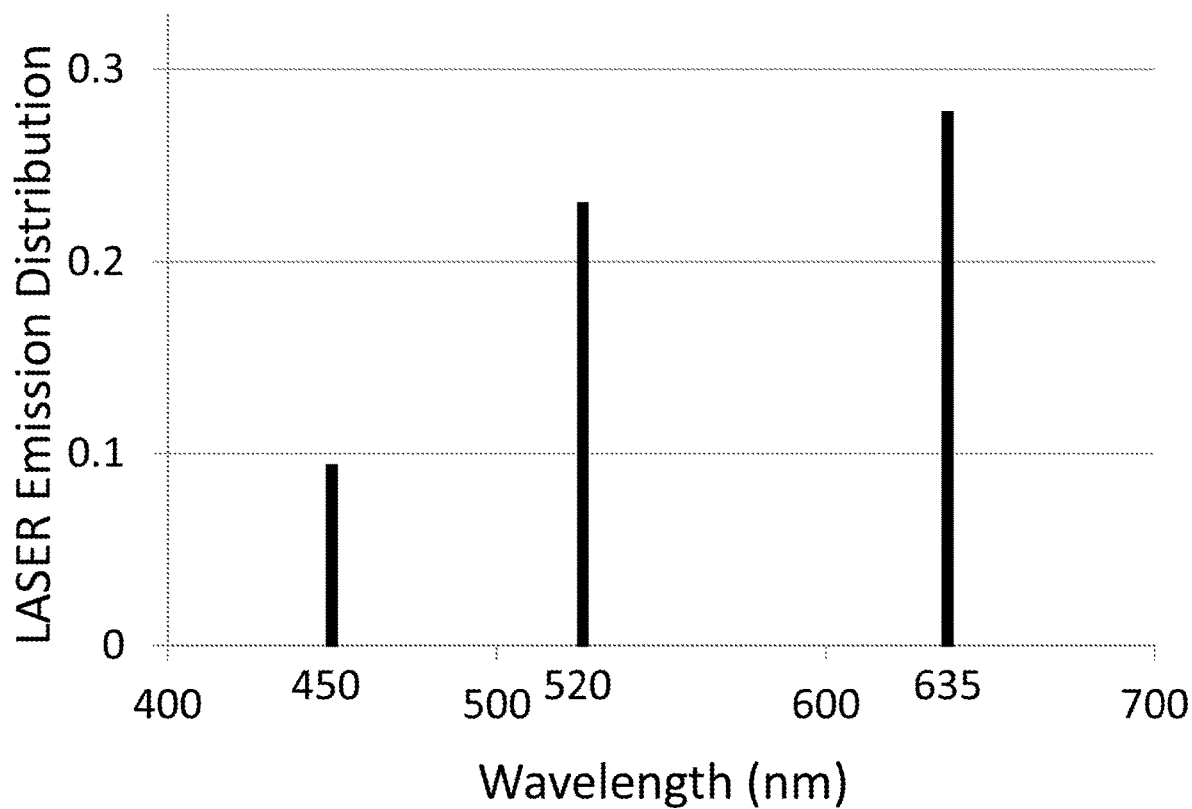
FIG. 5 shows a plot of the emission spectrum for an ophthalmic illumination source that uses a blue laser at 450 nm, a green laser, and a red laser.

To illustrate the improved safety provided to the physician by the ophthalmic illumination sources disclosed herein, FIGS. 6-7 each show the spectrum for an example of such an ophthalmic illumination source in which a laser having a narrow emission peak at 488 nm provides the shortest wavelength contributions to the illumination beam, and FIGS. 3-5 show spectra of alternative illumination sources that are compared below with the examples of FIGS. 6-7.

A conventional ophthalmic illumination system may use a xenon light source. FIG. 3 shows a plot 30 of the spectrum of light emitted by such a xenon light source as well as a plot 35 of that spectrum multiplied by the photopic luminosity function to provide a photopically corrected spectrum. The xenon light source spectrum is a broad continuum from about 435 nm to about 660 nm, with a bias to the blue-cyan. The blue-light retinal hazard is high for this light source, with about 20% of the power in the illumination beam (i.e., about 20% of the area under the xenon spectrum curve) at wavelengths below 480 nm.

Other conventional ophthalmic illumination systems may combine the output of up to four LEDs to provide an illumination beam. FIG. 4 shows a plot 40 of the spectrum from such an illumination source employing an LED with an emission peak at about 465 nm, another with an emission peak at about 525 nm, another with an emission peak at about 590 nm, and another with an emission peak at about 635 nm. This figure also shows a plot 45 of the photopically corrected spectrum from this illumination source. About 13% of the power in the illumination beam (i.e., about 13% of the area under the illumination source spectrum) is at wavelengths below 480 nm.

FIG. 5 shows a plot of the spectrum from an ophthalmic illumination source that combines the output from a blue laser with an emission peak at 450 nm, a green laser with an emission peak at 520 nm, and a red laser with an emission peak at 635 nm to provide an illumination beam. If the output power from each of these lasers is adjusted so that the illumination beam has a color temperature of about 4000 K, about 17% of the power in the illumination beam is at wavelengths below 480 nm.

Figure 6:
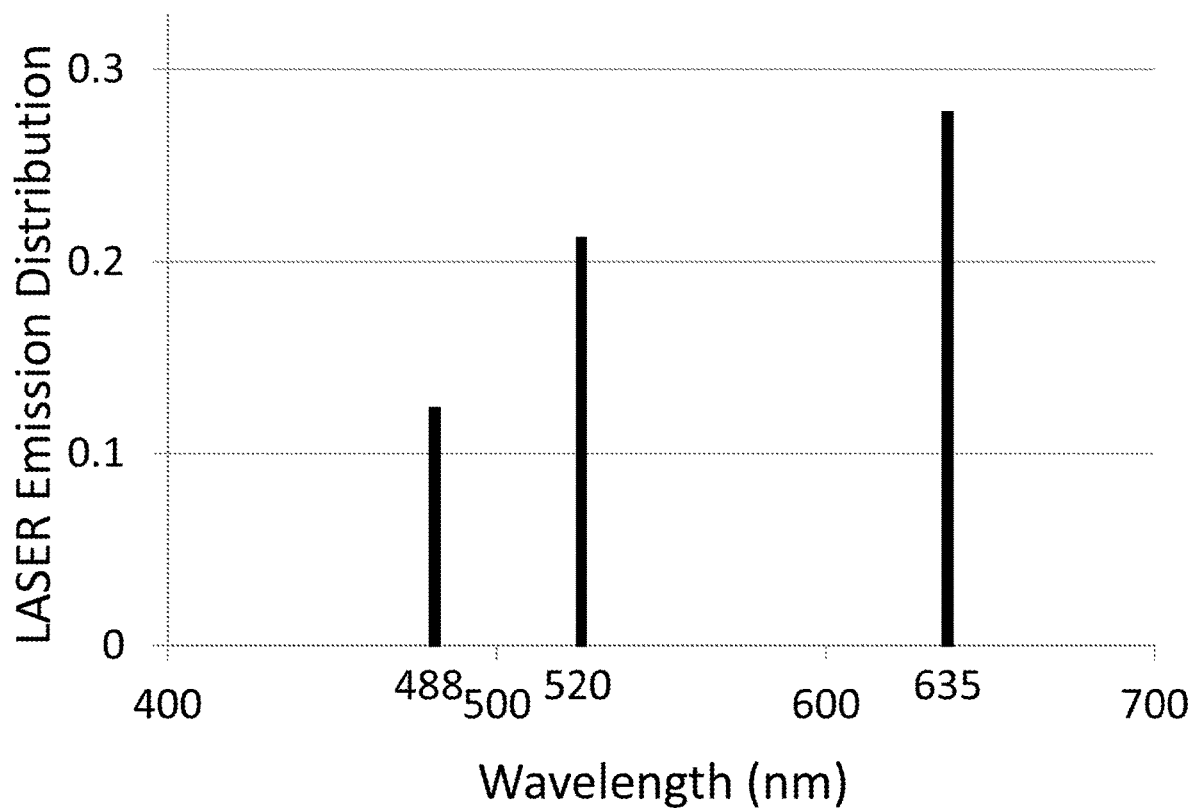
FIG. 6 shows a plot of the emission spectrum from an example physician and patient-safe ophthalmic illumination source as disclosed herein that uses a laser at 488 nm, a green laser, and a red laser.

FIG. 6 shows a plot of the spectrum from an example physician and patient-safe ophthalmic illumination source as disclosed herein. This illumination source combines the output from a narrow band laser with a peak at 488 nm, a laser with a peak at 520 nm, and a laser with a peak at 635 nm. If the output power from each of these lasers is adjusted so that the illumination beam has a color temperature of about 4000 K, only about 0.2% of the power in the illumination beam is at wavelengths below 480 nm.

Figure 7:
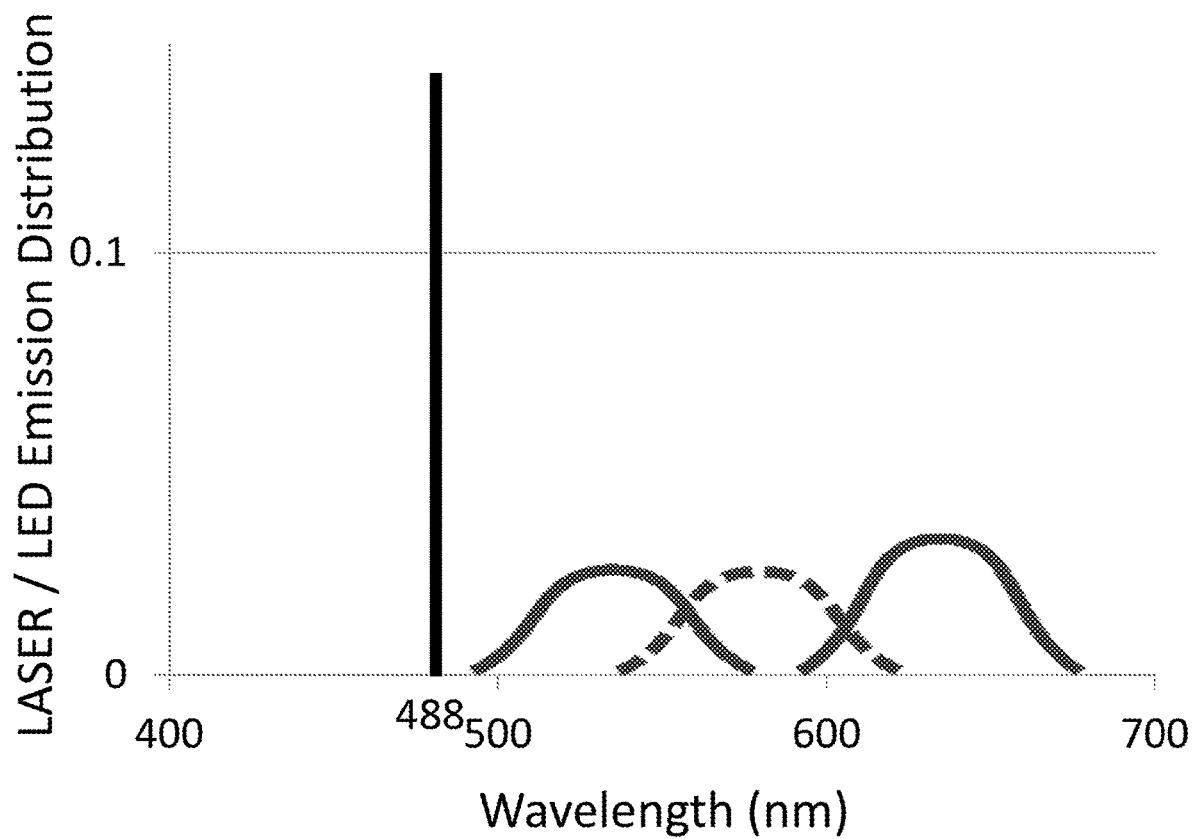
FIG. 7 shows a plot of the emission spectrum from an example physician and patient-safe ophthalmic illumination source as disclosed herein that uses a laser at 488 nm, a green LED, an optional orange LED, and a red LED.

FIG. 7 shows a plot of the spectrum from another example physician and patient-safe ophthalmic illumination source as disclosed herein. This illumination source combines the output from a narrow band laser with a peak at 488 nm, a green LED with a peak at about 525 nm, and a red LED with a peak at about 635 nm. The dashed line indicates emission from an optional orange LED with a peak at about 590 nm. If the output power from the laser and from each of the LEDs is adjusted so that the illumination beam has a color temperature of about 4000 K, only about 1.0% of the power in the illumination beam is at wavelengths below 480 nm.

Table 1 summarizes the relative blue light hazard and maximum exposure limit for the physician for the five example ophthalmic illuminators described above, if they are each operated to provide a white illumination beam with a color temperature of about 4000 K and the same perceived color and brightness (luminous flux) of about 20 lumens. As is apparent from Table 1, ophthalmic illuminators as disclosed herein in which the shortest wavelength light source contributing to the illumination beam has narrow band peak emission at $\lambda \geq$ about 480 nm (as in the examples of FIGS. 6-7) present significantly less blue light retinal hazard to the physician than alternative ophthalmic illuminators. In particular, physicians may be able to perform ophthalmic surgery essentially all day without concern for blue-light photochemical retinal hazard.

Although the example ophthalmic illuminator of FIG. 6 combines the output from narrow band lasers having peaks at 488 nm, 520 nm, and 635 nm, more generally ophthalmic illuminators as disclosed herein in which the shortest wavelength light source contributing to the illumination beam has narrow band peak emission at $\lambda \geq$ about 480 nm may comprise, for example, a narrow band laser having peak emission at about 480 nm to about 495 nm, a green laser having peak emission at about 510 nm to about 525 nm, and a red laser having peak emission at about 630 nm to about 650 nm.

Alternatively, ophthalmic illuminators as disclosed herein in which the shortest wavelength light source contributing to the illumination beam has narrow band peak emission at greater than or equal to about 480 nm may comprise, for example, a narrow band laser having peak emission at about 480 nm to about 495 nm, a green LED having peak emission at about 510 nm to about 550 nm, and/or an orange LED having peak emission at about 570 nm to about 610 nm, and/or a red LED having peak emission at about 620 nm to about 660 nm.

Other variations of ophthalmic illuminators as disclosed herein in which the shortest wavelength light source contributing to the illumination beam has narrow band peak emission at $\lambda \geq$ about 480 nm may comprise, for example, a narrow band laser having peak emission at about 480 nm to about 495 nm, and any suitable combination of one or more longer wavelength lasers and/or one or more longer wavelength LEDs.

Optionally, for ophthalmic illuminators as disclosed herein the output powers and/or the wavelengths of one or more of the light sources contributing to the illumination beam may be selected and/or optionally varied to control the apparent color of the illumination beam. For example, the illumination beam may be selected to appear white, or a tinted white, to a human having normal color vision. The illumination beam may have a color temperature in the range of about 2400 K to about 5500 K, for example.

An illumination beam having a green-tinted white color may be optimal for retinal surgery, for example. Such a green-tinted white illumination beam may be provided, for example, by combining the output of a narrow band laser having peak emission at about 480 nm to about 495 nm (e.g., at about 488 nm), a green laser having peak emission at about 510 nm to about 525 nm (e.g., at about 515 nm or about 520 nm), and a red laser having peak emission at about 630 nm to about 650 nm (e.g., at about 635 nm), with the lasers operated so that the output power of the laser having peak emission at about 510 nm to about 525 nm is greater than the output power of the laser having peak emission at about 480 nm to about 495 nm and greater than the output power of the laser having peak emission at about 630 nm to about 650 nm.

Optionally, the output power of each light source may be controlled independently by the physician to adjust the apparent color of the illumination beam. Further, an ophthalmic illuminator may be configured with one or more pre-set options providing illumination beams of pre-set apparent colors.

An advantage of using lasers as light sources in physician-safe ophthalmic illuminators as described above is that their light is emitted from a relatively small area (e.g., compared to LEDs or xenon lamps) and is therefore relatively efficiently coupled into a small diameter optical fiber core and transmitted through the optical fiber for use in illuminating tissue. Consequently, variations of the physician-safe ophthalmic illuminators disclosed herein may provide illumination beams that are efficiently coupled into, for example, 20 to 31-gauge optical fiber illumination probes, illumination chandeliers up to 34-gauge, and 20 to 27-gauge illuminated infusion probes, to deliver 20 lumens or more of light to the tissue to be illuminated. For example, an illumination beam from a physician-safe ophthalmic illuminator utilizing three lasers, as described above (e.g., the example of FIG. 6), may be delivered through a 30-gauge (310 micron outside diameter) probe with a (150 micron) plastic fiber with a numerical aperture of 0.5 in part enclosed in a metal sheath, or a direct 34-gauge (180 microns) plastic fiber with a numerical aperture of about 0.5, to provide 20 lumens of illumination. Small fibers such as a 34-gauge (180 micron outside diameter) probe with an 83 microns plastic fiber in part enclosed in a metal sheath are also possible with delivery of less than 20 lumens of illumination.

Figure 8:
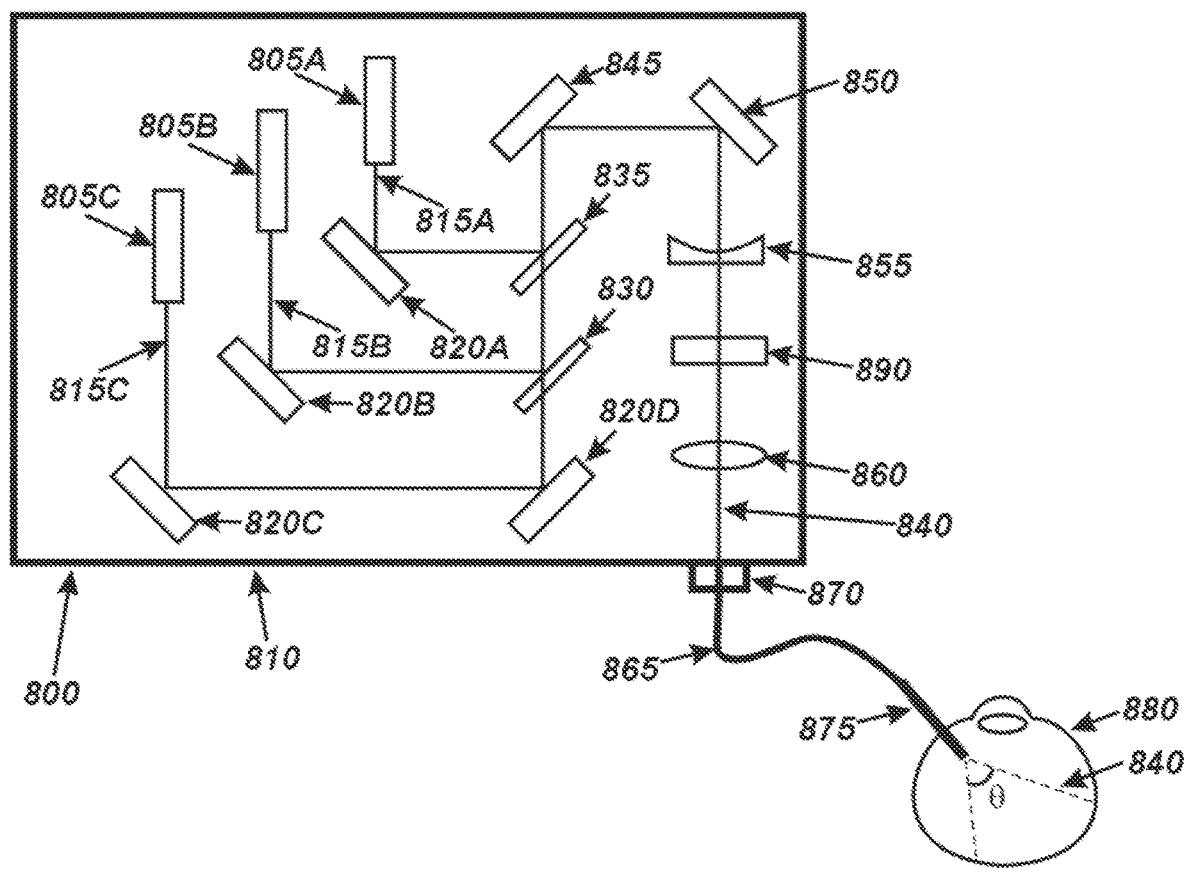
FIG. 8 shows an example ophthalmic illumination device optically coupled to an optical fiber probe inserted into an eye to provide illumination for an ophthalmic procedure.

Referring now to FIG. 8, an example ophthalmic illuminator 800 comprises three visible light lasers 805A-805C disposed within a housing 810. Light beams 815A-815C emitted by these lasers are combined collinearly by beam steering optics 820A-820D and dichroic mirrors 830 and 835 to form illumination beam 840. Additional beam steering optics 845 and 850 direct illumination beam 840 through lenses 855 and 860, which focus illumination beam 840 into the core portion of optical fiber 865. One end of optical fiber 865 is connected to the illuminator 800 with connector 870. The other end of optical fiber 865 is connected to a probe 875 adapted for insertion into an eye 880 (optical fiber 865 and probe 875 are together an optical fiber probe). Illumination beam 840 is emitted from the end of probe 875 with a cone angle θ to illuminate internal portions of the eye. An optional diffuser 890 located between lenses 855 and 860 reduces or eliminates laser speckle that might otherwise be visible to the physician on the tissue illuminated by the illumination beam.

Other methods or mechanisms for reducing laser speckle may also optionally be used. For example, one or more optical elements in the optical path from the lasers to the optical fiber may be configured to oscillate at greater than or equal to about 30 Hertz over a distance or angular range sufficient to translate speckles in the speckle pattern by at least one speckle diameter. This blurs the speckles to smooth out the intensity pattern as observed by a human observer having normal visual response.

Lasers 815A-815C may be semiconductor diode lasers, for example. Ophthalmic illuminator 800 may include power monitors arranged to monitor the output power of lasers 815A-815C. The power monitors may be integral with the lasers, for example. Beam steering optics 820A-820D, 845, and 850 may be any suitable refractive, reflective, or partially reflective optical elements. Lenses 855 and 860 may have any suitable focal lengths. Any other suitable optical arrangement for combining the output of lasers 815A-815C to form an illumination beam and coupling the illumination beam into optical fiber 865 may also be used.

A first one of lasers 805A-805C (e.g., laser 805A) is a narrow band laser having an emission peak at λ≥ about 480 nm. This laser provides the shortest wavelength contribution to the illumination beam. The second and third lasers may be, for example, a green laser and a red laser as described above. In other variations either or both of the second and third lasers may be replaced by one or more LEDs, as described above. More generally, the first laser may be used with any suitable combination of lasers or LEDs emitting at longer wavelengths than the first laser to form the illumination beam.

Ophthalmic illuminator 800 may be used in combination with a therapeutic laser beam which is delivered via a separate therapeutic optical fiber probe. The therapeutic laser beam may have a wavelength of about 532 nm, for example, which is conventional for retinal photocoagulation surgeries. Alternatively, the therapeutic laser beam may have a wavelength of about 561 nm, or about 577 nm, or any other suitable wavelength.

An observer may use a microscope to observe a surgical procedure in an eye performed using a therapeutic laser beam under illumination with an illumination beam provided by ophthalmic illuminator 800. In such cases the microscope may comprise a conventional microscope objective and a conventional eyepiece. In addition, the microscope may include an optical filter configured to block transmission of the light from the therapeutic laser beam while passing all or substantially all of the spectral components of the illumination beam.

This disclosure is illustrative and not limiting. Further modifications will be apparent to one skilled in the art in light of this disclosure and are intended to fall within the scope of the appended claims.

TABLE 1

| Ophthalmic Illuminator | Relative Blue Light Retinal Hazard | Maximum Exposure Limit for Physician |
|---|---|---|
| FIG. 3: Xenon | 4.4 | 1.6 hours |
| FIG. 4: LEDs at 465 nm, 525 nm, 590 nm, and 635 nm. | 2.9 | 2.4 hours |
| FIG. 5: Lasers at 450 nm, 520 nm, and 635 nm | 6.2 | 1.1 hours |
| FIG. 6: Lasers at 488 nm, 520 nm, and 635 nm | 1.0 | 7.0 hours |
| FIG. 7: Laser at 488 nm, green LED at 525nm, red LED at 635 nm. | 1.5 | 4.6 hours |

What is claimed is:

1. An illumination device comprising:
   a housing;
   a first diode laser positioned within the housing and having peak emission at a wavelength in the range of 480 nm to 495 nm with a full width half maximum of 2 nm to 10 nm;
   a second diode laser having peak emission at a green wavelength; and
   a third diode laser having peak emission at a red wavelength;
   an optical fiber connector attached to the housing;
   one or more lenses; and
   beam combining and beam steering optical elements arranged to combine an output beam from the first diode laser, an output beam from the second diode laser, and an output beam from the third diode laser to form an illumination beam and direct the illumination beam through the one or more lenses to focus into a core of an optical fiber externally attached to the optical fiber connector;
   wherein the illumination device does not comprise a light source having a peak emission at a wavelength less than 480 nanometers that is combined with the output beams from the first diode laser, the second diode laser, and the third diode laser to form the illumination beam; and
   wherein the apparent color of the illumination beam is selectable to a white or tinted white and a color temperature of the white apparent color is selectable from multiple color temperatures in the range 2400 K to 5500 K by supplying different relative powers of the output beams from the first, second, and third diode lasers.

2. The illumination device of claim 1, wherein the output beams are combined collinearly to form the illumination beam.

3. The illumination device of claim 1, wherein the color of the illumination beam is green-tinted white.

4. The illumination device of claim 1, wherein an end of the optical fiber not attached to the housing is adapted for insertion into a human eye.

5. The illumination device of claim 1, wherein the second diode laser has peak emission at a wavelength in the range of 510 nm to 525 nm and the third diode laser has peak emission at a wavelength in the range of 630 nm to 650 nm.

6. The illumination device of claim 5, wherein the power in the illumination beam from the second diode laser is greater than the power in the illumination beam from the first diode laser and greater than the power in the illumination beam from the third diode laser.

7. The illumination device of claim 6, wherein the first diode laser has peak emission at 488 nm, the second diode laser has peak emission at 515 nm, and the third diode laser has peak emission at 635 nm.

8. The illumination device of claim 5, wherein the first diode laser has peak emission at 488 nm, the second diode laser has peak emission at 520 nm, and the third diode laser has peak emission at 635 nm.

9. The illumination device of claim 1, comprising a power monitor integral with the first diode laser arranged to monitor the optical output power of the first diode laser.

\* \* \* \* \*